United States Patent [19]

Turnbull

[11] Patent Number: 4,559,353
[45] Date of Patent: Dec. 17, 1985

[54] INSECTICIDALLY ACTIVE 2,6-DISUBSTITUTED BENZIMIDATE DERIVATIVES

[75] Inventor: Michael D. Turnbull, Berkshire, England

[73] Assignee: Imperial Chemical Industries PLC, London

[21] Appl. No.: 547,629

[22] Filed: Nov. 1, 1983

[30] Foreign Application Priority Data

Nov. 5, 1982 [GB] United Kingdom ............... 8231696

[51] Int. Cl.⁴ .................... A01N 43/40; C07D 213/64
[52] U.S. Cl. .................................... 514/346; 546/291; 564/52; 514/598
[58] Field of Search .......... 546/291; 424/263; 564/48, 52; 260/453.99; 514/346

[56] References Cited

U.S. PATENT DOCUMENTS 4,200,653 4/1980 Huff et al. ............................. 514/596

FOREIGN PATENT DOCUMENTS 0033231 8/1981 European Pat. Off. ............ 546/292
2818830 8/1979 Fed. Rep. of Germany ...... 546/291
2092587A 8/1982 United Kingdom ........... 260/453.99

Primary Examiner—Alan L. Rotman
Attorney, Agent, or Firm—Cushman, Darby & Cushman

[57] ABSTRACT

The present invention provides compounds of formula:

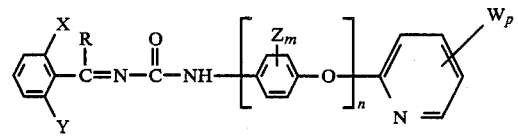

wherein X and Y are each independently selected from fluorine, chlorine, methyl or methoxy and one of X and Y may additionally be hydrogen; R is alkoxy of up to 6 carbon atoms, mono- or dialkylamino of up to 4 carbon atoms in the alkyl moiety, hydroxyamino, or alkoxyamino of up to 4 carbon atoms, m and p are independently selected from 1 to 4, and each W and each Z are independently selected from hydrogen, halo and haloalkyl containing 1 or 2 carbon atoms, and n is zero or one.

8 Claims, No Drawings

INSECTICIDALLY ACTIVE 2,6-DISUBSTITUTED BENZIMIDATE DERIVATIVES

This invention relates to compounds useful as insecticides, and their preparation.

U.S. Pat. No. 4,200,653 discloses a class of 2,6-difluorobenzimidate derivatives having insecticidal activity. These compounds are not very active against certain economically important pests at acceptable rates of application.

A preferred group of compounds are those wherein both X and Y are chloro or fluoro, Z and W are each selected from chloro, fluoro and trifluoromethyl and R is lower alkoxy of up to 4 carbon atoms, eg. ethoxy.

The following specific compounds are particularly illustrative of the compounds of the invention.

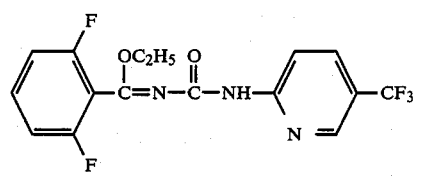

Compound I

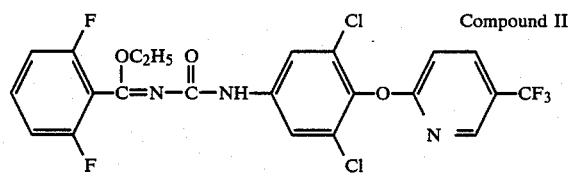

Compound II

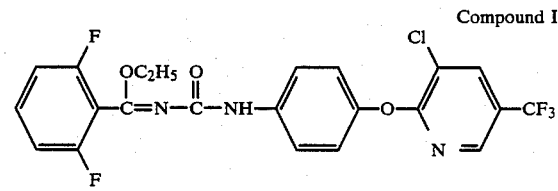

Compound III

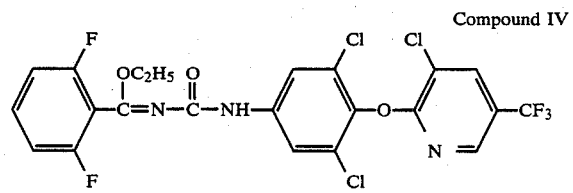

Compound IV

The compounds of the invention are capable of existing in two different geometrically isomeric forms, depending upon the spatial disposition of the substituent groups about the C=N— bond in the molecule. Following conventional chemical nomenclature, the two forms of a particular compound are designated as the E and the Z isomers of the compound. Referring to Compound I above, the E and Z forms are shown below by way of example.

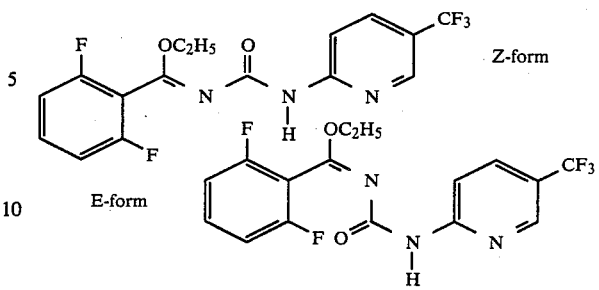

Depending upon the process chosen for preparing a particular compound, or on the way in which the conditions for a particular process are varied, either of the E and Z forms may be obtained, or a mixture of the two. The isomers, having different physical properties, may be separated by physical processes known in the chemical art. Both isomers of a particular compound have biological activity, but the biological effects of the isomers may not be completely identical in every case. The compounds herein are mixtures of E and Z forms unless otherwise specified.

The compounds of formula I may be used to combat and control infestations of insect pests particularly larval lepidopterous and coleopterous insects. The insect pests which may be combated and controlled by the use of the invention compounds include those pests associated with agriculture (which term includes the growing of crops for food and fibre products, horticulture and animal husbandry), forestry, the storage of products of vegetable origin, such as fruit, grain, timber, and also those pests associated with the transmission of diseases of man and animals. Thus the compounds may be used to control mosquito larvae and the larvae of the common housefly. The compounds may also be effective in controlling infestations of Coleoptera, Lepidoptera and Diptera by causing the laying of infertile eggs.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agent, dispersing agents and emulsifying agents may be of the cationic, anionic or non-ionic type. Suitable agents of the cationic type include, for example quaternary ammonium compounds, for example, cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonates. Suitable agents of the non-ionic type include for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane. The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying. The rate of application will depend upon factors such as the insect species to be controlled but in general a rate of from 10 g to 5 kg per hectare will be appropriate.

The compositions of the invention are very toxic to a variety of insect pests especially larval lepidopterous pests, including, for example, the following:
Plutella xylostella (diamond back moth, larvae)
Spodoptera littoralis (cotton leaf worm)
Heliothis virescens, Heliothis zea, and other Heliothis species.

The compounds of the invention may be prepared by reacting the imidate of formula:

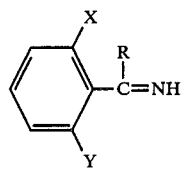

with the isocyanate of formula:

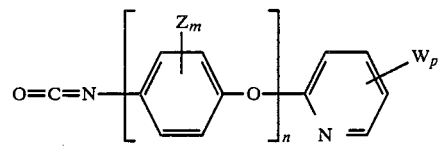

wherein X, Y, $R^1$, $R^2$, Z, m and n are as defined above, the process preferably taking place in an inert liquid diluent.

The isocyanates may be prepared from the corresponding amino compounds by reaction with phosgene, and the amino compounds may be prepared by reduction of the corresponding nitro compounds.

The complete reaction scheme is illustrated below for the preparation of Compound III as follows:

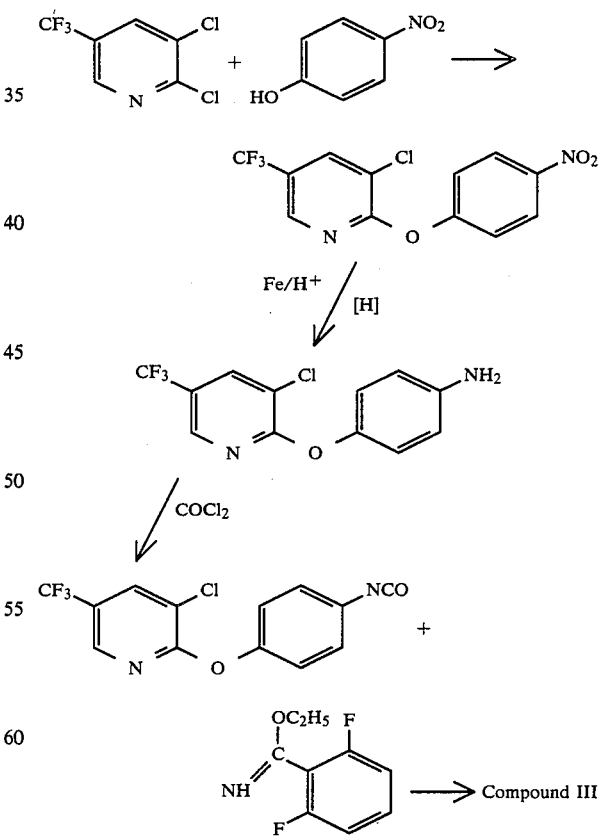

Further preparative details are given in Example 1 and 2 of the following Examples which serve to illustrate the various aspects of the invention.

EXAMPLE 1

This Example illustrates the preparation of ethyl N-[4-(3-chloro-5-trifluoromethylpyrid-2-yloxy)phenylcarbamoyl]-2,6-difluorobenzimidate (Compound III).

(a) 3-Chloro-5-trifluoromethyl-2-(4-nitrophenoxy)pyridine 2,3-Dichloro-5-trifluoromethylpyridine (2.16 g, 0.01M) and 4-nitrophenol (1.53 g, 0.011M) were mixed in methyl ethyl ketone (10 ml) containing anhydrous potassium carbonate (2.0 g) and heated at the reflux temperature for 10 hours. The cooled mixture was filtered to remove the solid matter and the filtrate concentrated by evaporation of the solvent under reduced pressure. The residue was triturated with diethyl ether and 3-chloro-5-trifluoromethyl-2-(4-nitrophenoxy)pyridine collected as a buff coloured solid (0.75 g), m.p. 98°–100° C.

(b) 2-(4-Aminophenoxy)-3-chloro-5-trifluoromethylpyridine

A mixture of 3-chloro-5-trifluoromethyl-2-(4-nitrophenoxy)pyridine (1.0 g), iron powder (3.2 g), isopropyl alcohol (60 ml), water (6 ml) and dilute hydrochloric acid (0.2 ml of a 2N solution), were heated at the reflux temperature for 12 hours. After cooling and filtering to remove the solid matter, the filtrate was concentrated by evaporation of the volatile portion under reduced pressure. The residual solid was recrystallised from n-hexane to yield 2-(4-aminophenoxy)-3-chloro-5-trifluoromethylpyridine (0.73 g) m.p. 85°–87° C.

$C_{12}H_8ClF_3N_2$ requires C, 50.50; H, 2.78; N, 9.71%. found C, 50.34; H, 2.69; N, 9.67%.

(c) 3-Chloro-5-trifluoromethyl-2-(4-isocyanatophenoxy)pyridine

A mixture of 2-(4-aminophenoxy)-3-chloro-5-trifluoromethylpyridine (0.45 g) and a solution of phosgene in toluene (50 ml of a 12% solution) was heated at the reflux temperature for 6 hours. Evaporation of the volatile portion under reduced pressure yielded 3-chloro-5-trifluoromethyl-2-(4-isocyanatophenoxy)pyridine as a residual pale brown oil (0.5 g) which was used without further purification.

(d) Ethyl 2,6-difluorobenzimidate

A mixture of triethyloxonium tetrafluoroborate (8.0 g, 0.042M), 2,6-difluorobenzamide (5.62 g, 0.036M) and methylene chloride was stirred at 20° C. for 18 hours, after which an excess of aqueous sodium bicarbonate solution was added. The methylene chloride phase was separated and dried over anhydrous magnesium sulphate. Evaporation of the solvent under reduced pressure yielded ethyl 2,6-difluorobenzimidate as a pale yellow oil (6.0 g) which was used without further purification.

(e) Ethyl N-[4-(3-chloro-5-trifluoromethylpyrid-2-yloxy)phenylcarbamoyl]-2,6-difluorobenzimidate A mixture of ethyl 2,6-difluorobenzimidate (0.14 g), 3-chloro-5-trifluoromethyl-2-(4-isocyanatophenoxy)pyridine (0.24 g), and diethyl ether (10 ml) was stirred at 20° C. for 18 hours, after which the solvent was removed by evaporation and the residual solid recrystallised from petroleum ether (boiling range 60°–80° C.) to yield ethyl N-[4-(3-chloro-5-trifluoromethylpyrid-2-yloxy)phenylcarbamoyl]-2,6-difluorobenzimidate as a white solid (0.29 g), m.p. 127°–130° C.

$C_{22}H_{15}ClF_5N_3O_3$ requires C, 52.90; H, 3.02; N, 8.41%. found C, 52.96; H, 3.01; N, 8.19%.

EXAMPLE 2

In a similar manner to that described in step (e) of Example I ethyl 2,6-difluorobenzimidate is reacted with 3-chloro-5-trifluoromethyl-2-(2,6-dichloro-4-isocyanatophenoxy)pyridine to give ethyl N-[4-(3-chloro-5-trifluoromethylpyrid-2-yloxy)-3,5-dichlorophenylcarbamoyl]-2,6-difluorobenzimidate (Compound IV). The intermediate isocyanate is obtained by the procedure of step (c) of Example 1 from 2-(4-amino-2,6-dichlorophenoxy)-3-chloro-5-trifluoromethylpyridine. This compound is described in Japanese published patent application No. 79-125699 (Chemical Abstracts, vol. 92, 146618d).

By similar procedures ethyl N-(5-trifluoromethylpyrid-2-ylcarbamoyl)-2,6-difluorobenzimidate (compound I) may be obtained from 2-isocyanato-5-trifluoromethylpyridine, and ethyl N-[4-(5-trifluoromethylpyrid-2-yloxy)-3,5-dichlorophenylcarbamoyl]-2,6-difluorobenzimidate (Compound II) may be obtained from (2,6-dichloro-4-isocyanatophenoxy)-5-trifluoromethylpyridine.

EXAMPLE 3

This Example illustrates the insecticidal properties of compound III as a representative compound according to the invention.

Freshly picked cabbage leaves were sprayed to run off with a composition containing 1000 parts per million of compound III (prepared by diluting a solution of the compound in the minimum amount of a mixture of 1 part by volume of acetone and 1 part by volume of ethanol with water containing 0.01% by volume of a wetting agent, "Lissapol" NX (a condensate of nonyl phenol with ethylene oxide containing about 8 moles of ethylene oxide per mole of nonyl phenol).

When dry, the leaves were infested with 10 second instar *Plutella xylostella* larvae (caterpillars of the diamond back moth) and the number of dead and affected larvae assessed after 48 hours, 72 hours and 6 days. In this test all the larvae were observed to be dead after 48 hours.

The invention compounds are also useful in the control of pests of domestic animals eg. sheep, cattle, especially sheep blow fly *Lucilia sericata*.

I claim:

1. A compound of formula:

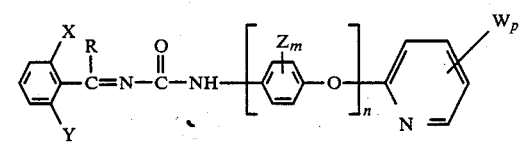

wherein X and Y are independently selected from fluorine, chlorine, methyl or methoxy and one of X and Y may additionally be hydrogen; R is alkoxy of up to 6 carbon atoms, mono or dialkylamino of up to 4 carbon atoms in the alkyl moiety, or alkoxyamino of up to 4 carbon atoms; m and p are independently selected from 1 to 4 and each W and each Z are independently selected from hydrogen, halo and haloalkyl containing 1 or 2 carbon atoms; and n is one.

2. A compound according to claim 1 wherein both X and Y are chloro or fluoro, Z and W are each selected from fluoro, chloro and trifluoromethyl and R is lower alkoxy of up to 4 carbon atoms.

3. A compound according to claim 2 wherein R is ethoxy.

4. Ethyl N-[4-(5-trifluoromethylpyrid-2-yloxy)-3,5-dichlorophenylcarbamoyl]-2,6-difluorobenzimidate.

5. Ethyl N-[4-(3-chloro-5-trifluoromethylpyrid-2-yloxy)phenylcarbamoyl]-2,6-difluorobenzimidate.

6. Ethyl N-[4-(3-chloro-5-trifluoromethylpyrid-2-yloxy)-3,5-dichlorophenylcarbamoyl]-2,6-difluorobenzimidate.

7. An insecticidal composition comprising an insecticidally effective amount of a compound according to claim 1 in association with an agriculturally and horticulturally acceptable diluent or carrier material.

8. A method of combating insect pests at a locus which comprises treating the locus with an insecticidally effective amount of a composition according to claim 7.

* * * * *